United States Patent [19]
Schlobohm

[11] Patent Number: 5,704,347
[45] Date of Patent: Jan. 6, 1998

[54] BREATHING VALVE

[75] Inventor: Joachim Schlobohm, Bad Oldesloe, Germany

[73] Assignee: Drägerwerik Aktiengesellschaft, Lübeck, Germany

[21] Appl. No.: 679,275

[22] Filed: Jul. 12, 1996

[30] Foreign Application Priority Data

Aug. 31, 1995 [DE] Germany ............ 195 32 042.5

[51] Int. Cl.$^6$ ............................................ A62B 9/02
[52] U.S. Cl. ............... 128/205.24; 128/201.28; 128/203.11; 128/206.15; 128/207.12
[58] Field of Search .................. 128/205.24, 201.28, 128/203.11, 206.15, 207.12; 137/535, 540, 543.23

[56] References Cited

U.S. PATENT DOCUMENTS

| | | | |
|---|---|---|---|
| Re. 32,553 | 12/1987 | Bennett et al. | 128/205.24 |
| 892,886 | 7/1908 | Prest | 137/535 |
| 973,512 | 10/1910 | Keeran | 137/535 |
| 1,287,419 | 12/1918 | Perry | 128/205.24 |
| 1,669,007 | 5/1928 | McMillan | 137/535 |
| 2,841,142 | 7/1958 | Hay | 128/205.24 |
| 2,848,157 | 8/1958 | Ayling | 137/535 |
| 2,895,503 | 7/1959 | Kolthoff, Jr. | 137/535 |
| 3,070,122 | 12/1962 | Weatherhead et al. | 137/535 |
| 3,528,342 | 9/1970 | Simcock | 137/535 |
| 3,783,894 | 1/1974 | Davison | 137/535 |
| 4,190,045 | 2/1980 | Bartels | 128/205.24 |
| 4,298,023 | 11/1981 | McGinnis | 137/535 |
| 4,354,931 | 10/1982 | Allori et al. | 137/535 |
| 4,865,250 | 9/1989 | Zaveri et al. | 137/535 |

FOREIGN PATENT DOCUMENTS 730 002   7/1937   Germany.
28 51 192 C2  11/1978  Germany.

*Primary Examiner*—Aaron J. Lewis
*Attorney, Agent, or Firm*—McGlew and Tuttle

[57] ABSTRACT

A breathing valve with a valve disk lying on a valve crater and with a valve spring, which is in contact with the valve disk with a first spring portion and with a support surface with a second spring portion. The valve spring is designed as a valve spring that can be spread open against the support surface, and the support surface is designed as a wedge-shaped spreading surface engaging the second spring portion in the area of contact with the second spring portion.

20 Claims, 3 Drawing Sheets

BREATHING VALVE

FIELD OF THE INVENTION

The present invention pertains to a breathing valve with a valve disk lying on a valve crater (seat) and with a valve spring, which is in contact with the valve disk with a first spring end and with a support surface with a second spring end.

BACKGROUND OF THE INVENTION

A breathing valve of this type has become known from DE-PS 730 002. A valve crater, a valve disk lying on the valve crater, and a valve spring pressing the valve disk against the valve crater are arranged in a valve housing. The end of the valve spring located opposite the valve disk is fastened to a flat support surface. The prior-art breathing valve is used as an expiration valve for gas masks. The disadvantage of the prior-art breathing valve is the fact that the valve disk tends to vibrate during the flow of gas through the valve, because the valve spring has hardly any damping properties.

Even though damping devices for reducing undesired vibrations of the valve have been known in connection with breathing valves, these devices either have a very complicated design or they change the opening characteristics of the valve. A breathing valve with a damping device is shown in, e.g., DE 28 51 192 C2.

SUMMARY AND OBJECTS OF THE INVENTION

The primary object of the present invention is to improve a breathing valve of the above-described type such that an accurate opening and closing of the valve is guaranteed.

According to the invention, a breathing valve is provided with a valve disk lying on a valve crater (seat) and with a valve spring. The valve spring is in contact with the valve disk with a first spring end and is in contact with a support surface with a second spring end. The valve spring is spread against the support surface, and the support surface provides a spreading surface engaging the second spring end in the area of contact with the second spring end.

The advantage of the present invention is essentially that vibrations of the valve are markedly or significantly reduced due to the spreading of the valve spring at a spreading surface engaging the end of the spring in a wedge-shaped manner and due to the associated sliding friction between the valve spring and the spreading surface. The value of the sliding friction is determined essentially by the coefficient of sliding friction. A coefficient of sliding friction that is favorable for suppressing the vibrations of the valve can be set by a friction means such as a corresponding surface treatment of the spreading surface or of the spring end that is in contact with the spreading surface, e.g., by roughing or polishing or by coating. Other variable parameters of the friction means are the slope angle and the shaping of the spreading surface. For example, a stepped design of the spreading surface is especially advantageous. The spreading of the valve spring leads, as another advantage of the present invention, to a degressive spring characteristic, which has an especially favorable effect on the expiration resistances in the case of massive gas flows.

The valve spring is advantageously designed as a leaf spring bent in the shape of a U, wherein the first spring end is located on an axis of symmetry of the bent part of the leaf spring and the opposite, second spring end is formed by the ends of the legs of the leaf spring which point away from the first spring end.

The spreading surface advantageously has a cylindrical area projecting in a stepped manner, which is directed toward the insides of the leg ends of the leaf spring, or is also in contact with the insides of the leg ends.

The spreading surfaces preferably form a slope angle $\alpha$ of 120° with the axis of symmetry of the breathing valve.

The leaf spring is preferably designed such that its radius of curvature R is approximately equal to the height H of the leaf spring. The length X of the leg of the leaf spring is about 40% of the height H of the leaf spring. The diameter D of the leaf spring is preferably selected to be such that it is about twice the height H of the leaf spring.

Sliding surfaces are advantageously provided at the leg ends of the leaf spring in the area of the sloping part of the spreading surface. These sliding surfaces may be designed, e.g., such that the leg ends of the leaf spring are bent over to the outside with a radius of curvature.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
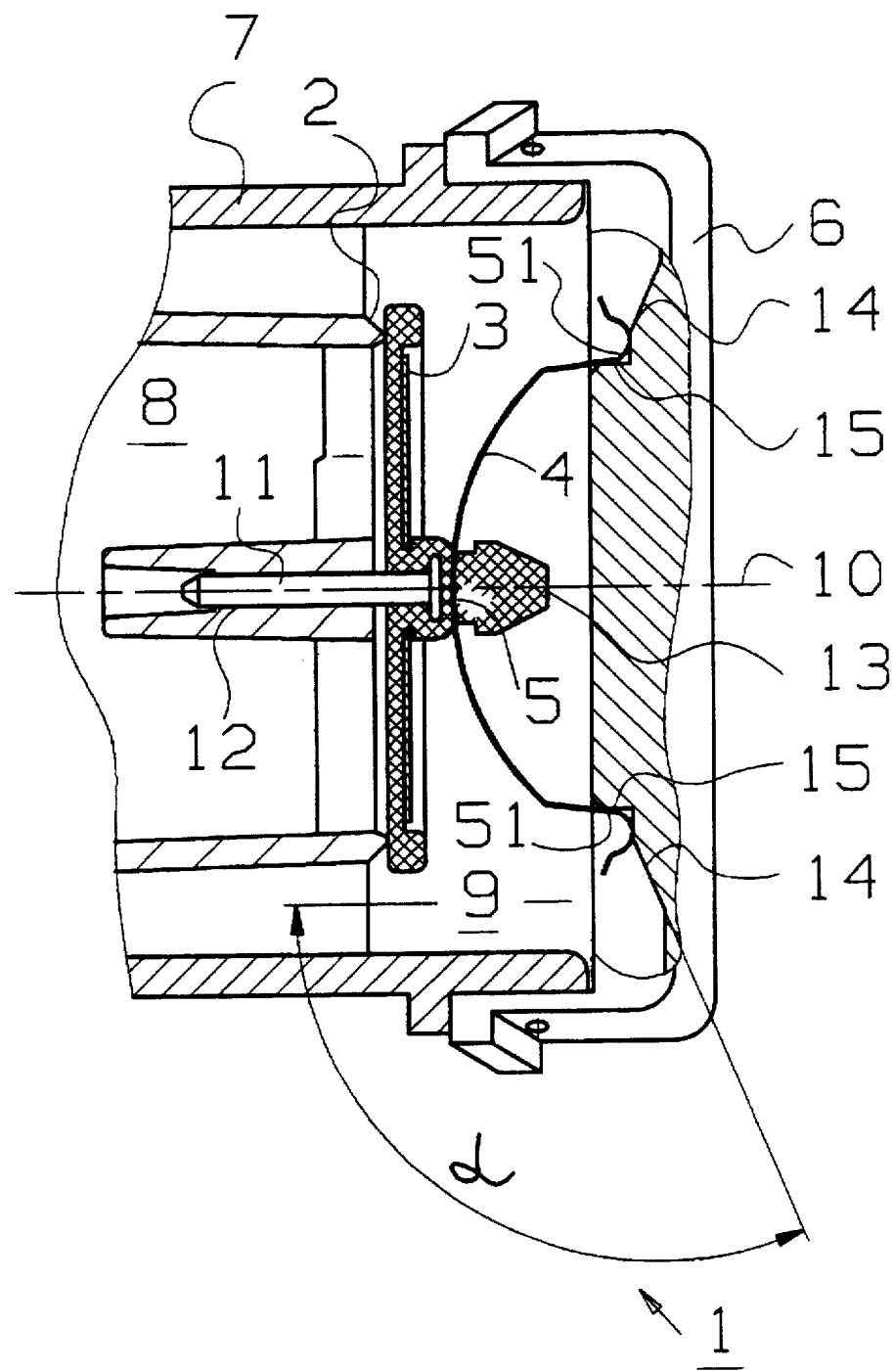
FIG. 1 is a longitudinal sectional view of a breathing valve.

FIG. 1 shows a longitudinal section of a breathing valve 1 with a valve crater 2, with a valve disk 3 lying on the valve crater 2, and with a leaf spring 4, which presses the valve disk 3 against the valve crater 2 with a first spring leg 5 and whose leg ends 51 are supported as a second spring end against a spring bridge 6 acting as a support surface. The valve crater 2 and the valve disk 3 are arranged coaxially in a valve housing 7, to which the spring bridge 6 is fastened. The gas flows through the breathing valve 1 from an inflow channel 8 via the valve disk 3 and into an outflow channel 9. A guide pin 11, which is axially displaceably accommodated in a guide hole 12 located within the valve crater 2, is fastened to the valve disk 3 along an axis of symmetry 10 of the breathing valve 1. It shall be achieved by means of the guide pin 11 that the valve disk 3 will be displaced in parallel to the sealing surface formed by the valve crater 2. A fastening button 13, to which the first spring portion or spring end 5 is fastened, is located on the side of the valve disk 3 facing away from the guide pin 11. The part of the spring bridge 6 directed into the outflow space of the valve housing 7 has wedge-shaped spreading surfaces 14 and a cylindrical area 15, which projects on the spreading surfaces 14 in a stepped manner and is in contact with the insides of the leg ends 51. The slope angle $\alpha$ of the spreading surfaces 14 against the axis of symmetry 10 is about 120°.

Figure 2:
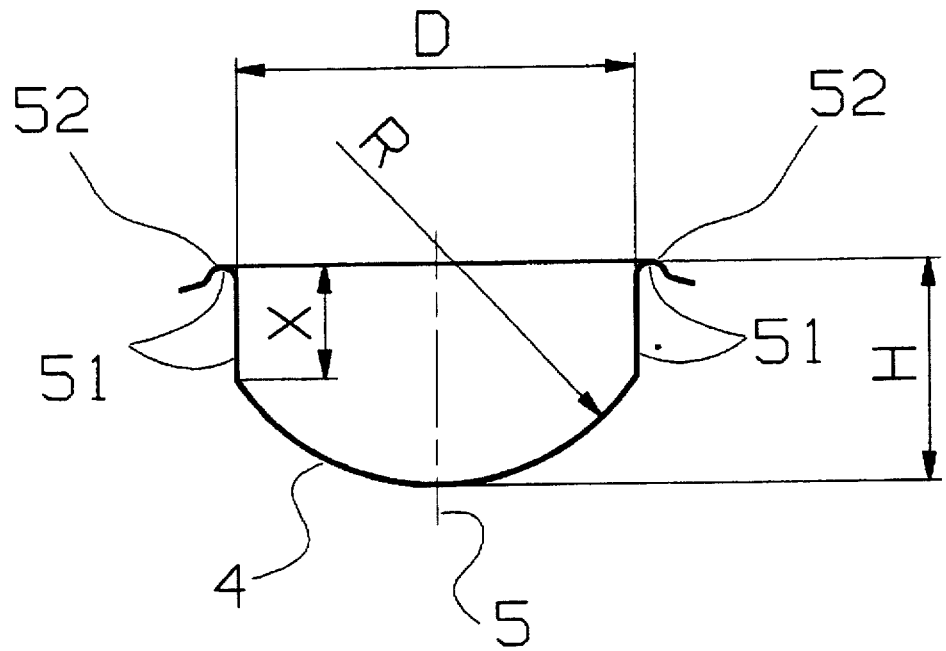
FIG. 2 is a side view of a valve spring of the breathing valve according to FIG. 1.

The dimensions of the leaf spring 4 are selected to be such that the height H of the leaf spring is approximately equal to the radius of curvature R, and the diameter D of the leaf spring FIG. 2 shows a side view of the leaf spring 4 according to FIG. 1. Identical components are designated with the same reference numbers as in FIG. 1. To improve the sliding properties of the spring ends 51 on the spreading surfaces 14 (FIG. 1), the leg ends 51, acting as sliding surfaces 52, are bent over to the outside. The diameter D of the leaf spring is twice the height H of the leaf spring. The leg length X of the leaf spring 4 approximately corresponds to 40% of the height H of the leaf spring.

Figure 3:
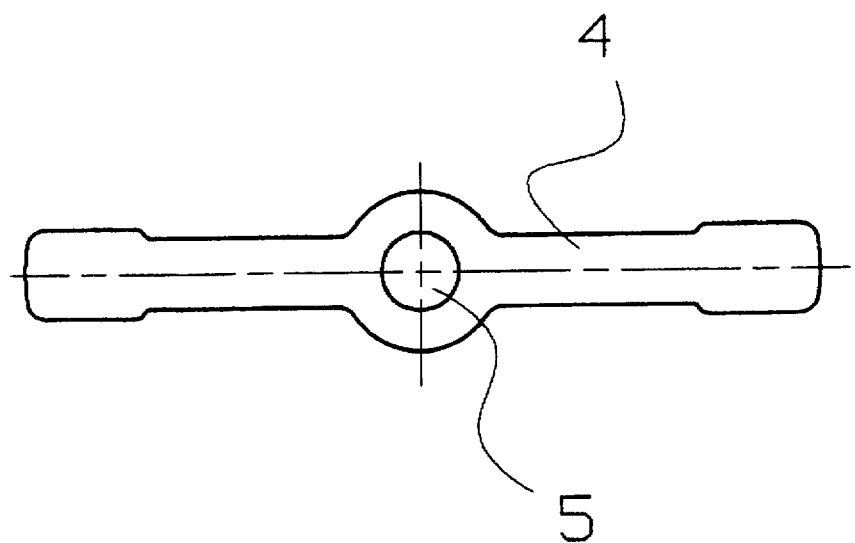
FIG. 3 is a top view of the valve spring according to FIG. 2, which is developed into the plane of the drawing.

FIG. 3 shows a top view of the leaf spring 4 developed into the plane of the drawing. The leaf spring 4 is made of chrome-nickel steel X 12 Cr Ni 177 and has a strength of one tenth of one mm. The width of the leaf spring 4 is about 3.5 mm.

Figure 4:
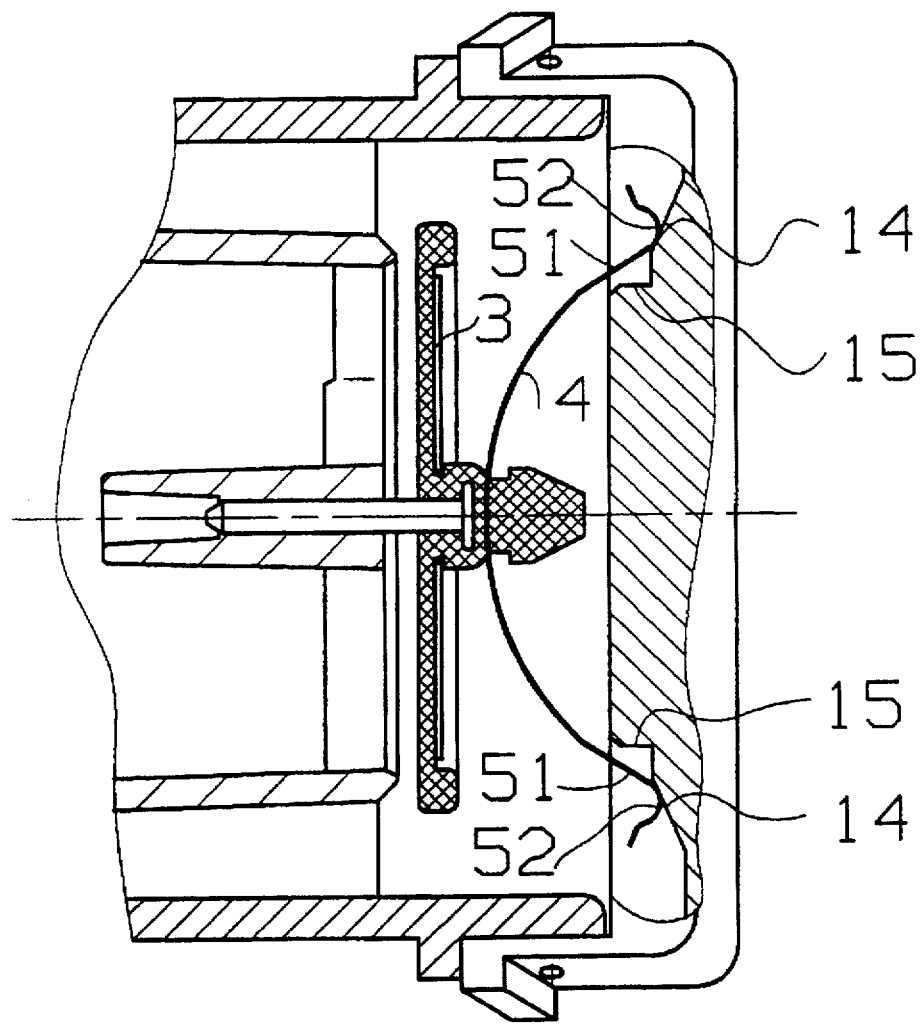
FIG. 4 is a sectional view of the breathing valve according to FIG. 1 in the open position.

FIG. 4 shows the breathing valve 1 according to FIG. 1 in the open position. Identical components are designated with the same reference numbers as in FIGS. 1 through 3. The leaf spring 4 is spread out during the opening movement of the valve disk 3 by the leg ends 51 sliding on the cylindrical area 15 and the sliding surfaces 52 of the leaf spring 4 sliding on the spreading surfaces 14. On the one hand, the spreading leads to a degressive spring characteristic, which results in especially low respiration resistances at massive gas flows, and, on the other hand, the tendency to vibrate is markedly reduced by the sliding friction between the leg ends 51 and the cylindrical area 15, and between the sliding surfaces 52 and the spreading surfaces 14, without any special measures for damping being necessary. In the case of certain deflections of the valve disk 3, it may also happen that only a sliding motion is possible between the spreading surfaces 14 and the sliding surfaces 52. This case is illustrated in FIG. 4.

While a specific embodiment of the invention has been shown and described in detail to illustrate the application of the principles of the invention, it will be understood that the invention may be embodied otherwise without departing from such principles.

What is claimed is:

1. A breathing valve, comprising:

a valve disk;

a valve crater, said valve disk lying on said valve crater;

a support surface;

a valve spring in contact with said valve disk with a first spring end and in contact with said support surface with a second spring end, said valve spring being spread against said support surface, said support surface defining a spreading surface engaging said second spring end in the area of contact with said second spring end; and friction means positioned in said second spring portion and in said support surface for creating a specific coefficient of friction that reduces vibration of said valve disk when a user of the breathing valve expirates through the breathing valve.

2. A breathing valve in accordance with claim 1, wherein said valve spring is a leaf spring bent in the shape of a U, wherein said first spring end is provided on an axis of symmetry of a bent part of said leaf spring and said second spring end is formed by leaf spring leg ends which extend away from said first spring end.

3. A breathing valve in accordance with claim 2, wherein; said friction means includes a shape of said spreading surface, and said shape includes a cylindrical area, which projects in a stepped manner, and is directed toward the insides of the said leg ends.

4. A breathing valve in accordance with claim 2, wherein; said friction means includes a shape angle α of said spreading surface of about 120° with said axis of symmetry.

5. A breathing valve in accordance with claim 2, wherein a radius of curvature R of said leaf spring and a height H of said leaf spring are approximately equal.

6. A breathing valve in accordance with claim 2, wherein said leaf spring has a leg length X corresponding to substantially 40% of a height H of said leaf spring.

7. A breathing valve in accordance with claim 2, wherein a diameter D of said leaf spring is about twice a height H of the said leaf spring.

8. A breathing valve in accordance with claim 2, wherein said leg ends have a sliding surface in an area of a sloping part of said spreading surface.

9. A breathing valve, comprising:

a valve disk;

valve crater means for defining a gas inflow channel and having an annular valve seat, said valve disk lying on said valve seat;

a support surface connected to said valve crater means;

a valve spring in contact with said valve disk with a first spring portion and in contact with said support surface with a second spring portion, said valve spring being spread against said support surface, said support surface defining a spreading surface engaging said second spring portion in the area of contact with said second spring end; and friction means positioned in said second spring portion and in said support surface for creating a specific coefficient of friction that reduces vibration of said valve disk when a user of the breathing valve expirates through the breathing valve.

10. A breathing valve in accordance with claim 9, wherein;

said friction means includes a slope angle α of said spreading of about 120° with said axis of symmetry.

11. A breathing valve in accordance with claim 9, wherein:

a shape of said support surface causes degressive spring characteristics in said valve spring.

12. A breathing valve in accordance with claim 9, wherein:

said friction means includes a specific surface treatment of a contact surface between said second spring portion and said support surface.

13. A breathing valve in accordance with claim 9, wherein:

said friction means includes a shape of said support surface.

14. A breathing valve in accordance with claim 9, wherein:

said friction means includes said shape of said support surface.

15. A breathing valve, comprising:

a valve disk;

valve crater means for defining a gas inflow channel and having an annular valve seat, said valve disk lying on said valve seat;

a support surface connected to said valve crater means;

a valve spring having a first spring portion in contact with said valve disk, said valve spring having a second spring portion in contact with said support surface, said valve spring biasing said valve disk against said valve seat, said support surface having a shape for spreading said second spring portion when said valve disk moves away from said valve seat;

friction means at said second spring portion and at said support surface for creating a specific coefficient of friction that reduces vibration of said valve disk when an operator of the breathing valve expirates through the breathing valve.

16. A breathing valve in accordance with claim 15, wherein:

said specific coefficient of friction markedly reduces vibration of said valve disk.

17. A breathing valve in accordance with claim 15, wherein:

said shape of said support surface causes degressive spring characteristics in said valve spring for especially low respiration resistances at massive gas flows.

18. A breathing valve in accordance with claim 17, wherein: said friction means includes said shape of said support surface.

19. A breathing valve in accordance with claim 15, wherein:

said friction means includes a specific surface treatment of a contact surface between said second spring portion and said support surface.

20. A breathing valve in accordance with claim 15, wherein:

said friction means includes said shape of said support surface.

* * * * *